(12) United States Patent
Osaka et al.

(10) Patent No.: US 10,905,435 B2
(45) Date of Patent: Feb. 2, 2021

(54) ENDOSCOPE TREATMENT TOOL

(71) Applicant: OLYMPUS CORPORATION, Hachioji (JP)

(72) Inventors: Shingo Osaka, Tokyo (JP); Tomohiro Tsuji, Tokyo (JP); Tomohiko Mamiya, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 213 days.

(21) Appl. No.: 16/236,692

(22) Filed: Dec. 31, 2018

(65) Prior Publication Data
US 2019/0133597 A1    May 9, 2019

Related U.S. Application Data

(63) Continuation of application No. PCT/JP2016/070426, filed on Jul. 11, 2016.

(51) Int. Cl.
*A61B 17/12* (2006.01)
*A61B 17/128* (2006.01)
(Continued)

(52) U.S. Cl.
CPC ...... *A61B 17/1285* (2013.01); *A61B 17/1227* (2013.01); *A61B 2017/293* (2013.01); *A61B 2017/2929* (2013.01)

(58) Field of Classification Search
CPC ............ A61B 17/1285; A61B 17/1227; A61B 17/128; A61B 17/122; A61B 17/0482;
(Continued)

(56) References Cited

U.S. PATENT DOCUMENTS

| | | | | |
|---|---|---|---|---|
| 2008/0140089 A1* | 6/2008 | Kogiso | ............. | A61B 17/1285 606/142 |
| 2009/0275959 A1 | 11/2009 | Cui et al. | | |
| 2011/0054498 A1* | 3/2011 | Monassevitch | .... | A61B 17/1285 606/142 |

FOREIGN PATENT DOCUMENTS

| EP | 2 995 262 A1 | 3/2016 |
|---|---|---|
| JP | 2010-012168 A | 1/2010 |

(Continued)

OTHER PUBLICATIONS

Oct. 4, 2016 International Search Report issued in International Patent Application No. PCT/JP2016/070426.

*Primary Examiner* — Erich G Herbermann
(74) *Attorney, Agent, or Firm* — Oliff PLC

(57) ABSTRACT

An endoscope treatment tool includes: a sheath; a clip unit; a biasing member arranged between a distal end part of the sheath and the clip unit; and a first rotation preventing part capable of preventing the clip unit from rotating relative to the distal end part of the sheath about a longitudinal axis. The clip unit includes: a clip body; a holding tube; and a second rotation preventing part capable of preventing the clip body from rotating relative to the holding tubes about the longitudinal axis. The biasing member biases the holding tube so as to separate from the distal end part of the sheath. When a proximal end part of the holding tube comes into contact with the distal end part of the sheath against the biasing force of the biasing member, the first rotation preventing part prevents the relative rotation of the clip unit.

5 Claims, 11 Drawing Sheets

(51) Int. Cl.
*A61B 17/122* (2006.01)
*A61B 17/29* (2006.01)

(58) Field of Classification Search
CPC . A61B 17/0487; A61B 17/08; A61B 17/1222;
A61B 2017/2929; A61B 2017/00818;
A61B 2017/00584; A61B 2017/0488;
A61B 2017/049; A61B 2017/1225; A61F 5/0086
See application file for complete search history.

(56) References Cited

FOREIGN PATENT DOCUMENTS

| | | |
|---|---|---|
| JP | 5750624 B2 | 7/2015 |
| WO | 2009/136397 A2 | 11/2009 |
| WO | 2014/181676 A1 | 11/2014 |

\* cited by examiner

ENDOSCOPE TREATMENT TOOL

CROSS REFERENCE TO RELATED APPLICATIONS

This application is a continuation application based on a PCT Patent Application No. PCT/JP2016/070426, filed on Jul. 11, 2016, the entire content of which is hereby incorporated by reference.

BACKGROUND OF THE INVENTION

Field of the Invention

The present invention relates to an endoscope treatment tool.

Description of the Related Art

Conventionally, an endoscopic treatment instrument (hereinafter also referred to as "treatment instrument"), which is a ligating apparatus having a clip unit, is used for ligating an opening or a blood vessel formed in a tissue. As such a treatment instrument, for example, a treatment instrument described in Japanese Patent No. 5750624 is known. The treatment instrument described in Japanese Patent No. 5750624 includes a clip unit and a treatment instrument main body to which a clip unit can be attached and detached at a distal end part. The clip unit has a clip body having an arm part and a holding tube accommodating a proximal end part of the clip body.

When the target tissue is ligated using the above-described treatment tool including the clip unit, the operation unit of the treatment instrument is operated to rotate the clip body so that the arm part faces an appropriate direction with respect to the target tissue. In this state, the clip body is pressed against the target tissue and the clip body is pulled into the holding tube to close the arm part and grasp the target tissue with the arm part.

SUMMARY

An endoscope treatment tool includes: a sheath having a longitudinal axis and formed in an elongated shape; a clip unit detachably connected to a distal end part of the sheath; an operation member inserted into the sheath so as to be able to advance and retreat and connected to the clip unit; a biasing member; and a first rotation preventing part configured so as to be able to prevent the clip unit from rotating relative to the distal end part of the sheath about the longitudinal axis. The clip unit includes: a clip body having a first arm part and a second arm part which are opposed to each other and whose distal end parts are arranged to be spaced apart from each other, the clip body being connected to the operation member and elastically deformable; a holding tube formed in a cylindrical shape and having a part of the clip body disposed therein; and a second rotation preventing part configured so as to be able to prevent the clip body from rotating relative to the holding tube about the longitudinal axis in an open state in which the first arm part and the second arm part are separated from each other. The biasing member biases the holding tube so as to separate from the distal end part of the sheath. When a proximal end part of the holding tube comes into contact with the distal end part of the sheath against the biasing force of the biasing member, the first rotation preventing part prevents the relative rotation of the clip unit.

The first rotation preventing part may include: a first engaging portion having a concave-convex shape and formed on a proximal end surface of the holding tube; and a second engaging portion having a concave-convex shape and formed on a distal end surface of the sheath, the second engaging portion being engageable with the first engaging portion. The proximal end surface of the holding tube may contact the distal end surface of the sheath, whereby the first engaging portion engages with the second engaging portion.

The first rotation preventing part may include: a third engaging portion having a concave-convex shape and formed on an outer peripheral surface of the holding tube; and a fourth engaging portion having a concave-convex shape and formed on an inner peripheral surface of the distal end part of the sheath, the fourth engaging portion being engageable with the third engaging portion. The proximal end part of the holding tube may enter inside of the distal end part of the sheath, whereby the third engaging portion engages with the fourth engaging portion.

The first rotation preventing part may have a slip prevention member provided on an inner peripheral surface of the distal end part of the sheath. The proximal end part of the holding tube may enter inside of the distal end part of the sheath, whereby the proximal end part of the holding tube engages with the slip prevention member.

The biasing member may be a coil spring disposed between the distal end part of the sheath and the holding tube.

The second rotation preventing part may have a first notch portion and a second notch portion that are provided at a peripheral edge part on a distal end side of the holding tube, the first notch portion and the second notch portion being disposed at positions opposed to each other across the longitudinal axis.

The first arm part may be arranged to pass through inside of the first notch portion.

The second arm part may be arranged to pass through inside of the second notch portion.

The second rotation preventing part may prevent the clip body from relatively rotating with respect to the holding tube about the longitudinal axis in a state in which the first arm part and the second arm part are the most distant from each other.

DETAILED DESCRIPTION OF THE PREFERRED EMBODIMENTS

First Embodiment

Hereinafter, an embodiment of the present invention will be described with reference to FIGS. 1 to 8.

Figure 1:
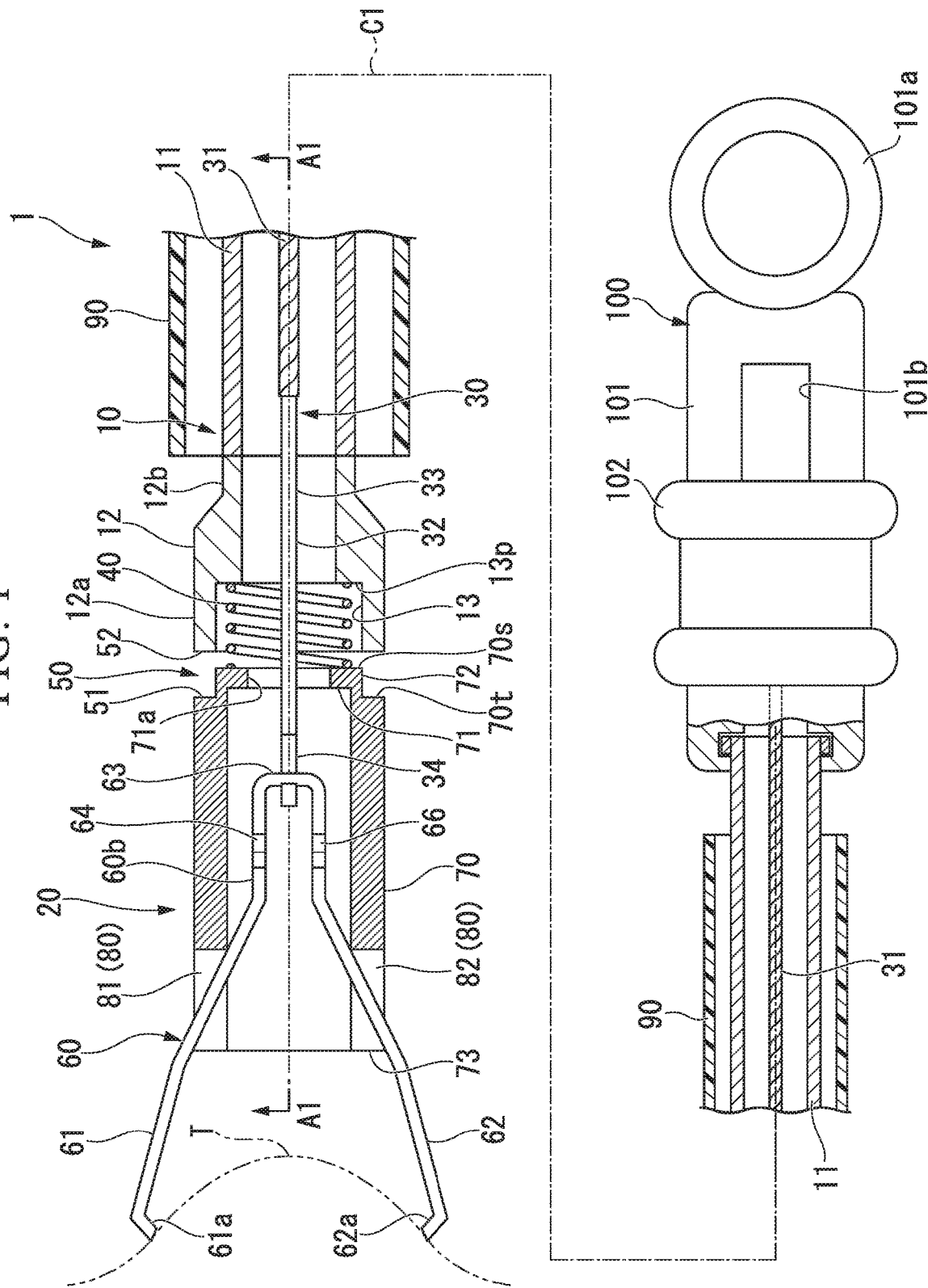
FIG. 1 is a partially broken view showing an endoscopic treatment tool according to one embodiment of the present invention.
Figure 2:
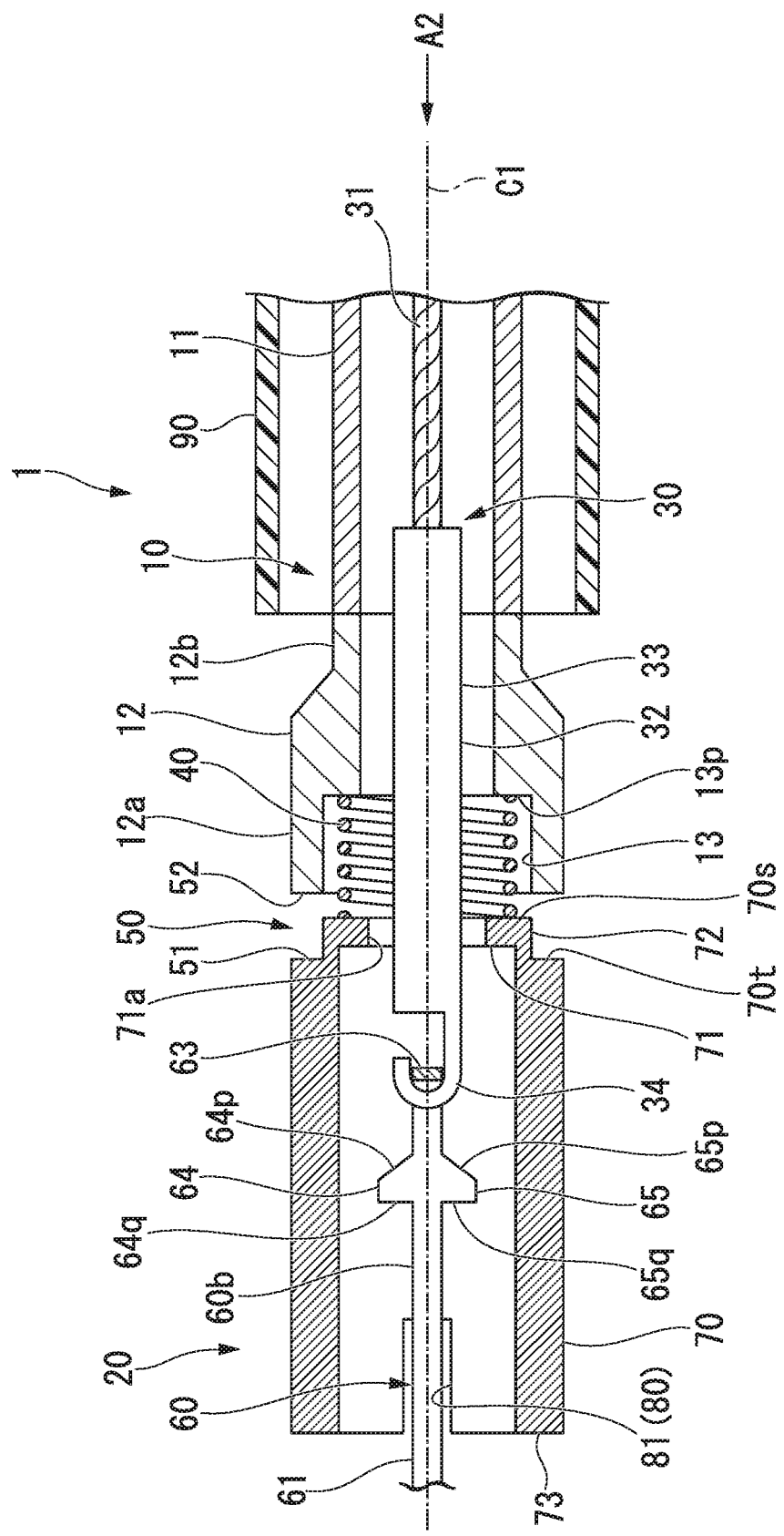
FIG. 2 is a cross-sectional view taken along the line A1-A1 of FIG. 1.

FIG. 1 is a side view showing the endoscopic treatment tool 1 partially broken away according to the present embodiment. FIG. 2 is a cross-sectional view taken along line A1-A1 of FIG. 1.

The endoscopic treatment instrument 1 includes a sheath 10, a clip unit 20, an operation member 30, a coil spring (biasing member) 40, and a first rotation preventing part 50.

The sheath 10 has an elongated shape having a longitudinal axis C1. The sheath 10 has a coil sheath 11 and a distal end member 12. The coil sheath 11 has flexibility and is formed in a cylindrical shape. As the coil sheath 11, a coil formed by winding a strand (not shown) in close winding along the longitudinal axis C1 can be used. In this case, the coil sheath 11 is resistant to compressive force in a direction along the longitudinal axis C1. The strand of the coil sheath 11 is made of stainless steel, for example.

The distal end member 12 is fixed to the distal end part of the coil sheath 11. The distal end member 12 is formed in a cylindrical shape, and is made of, for example, stainless steel. The inner cavity of the distal end member 12 communicates with the inner cavity of the coil sheath 11. The inner diameter of the proximal end part 12b of the distal end member 12 is set equal to the inner diameter of the coil sheath 11. The inner diameter of the distal end part 12a of the distal end member 12 is set to be larger than the inner diameter of the proximal end part 12b. As a result, a holding portion 13 for holding the coil spring 40 is formed at the distal end part 12a.

The holding portion 13 is formed so as to be recessed from the distal end surface of the distal end member 12 toward the proximal end side. Since the inner diameter of the distal end part 12a (the inner diameter of the holding portion 13) of the distal end member 12 is larger than the inner diameter of the proximal end part 12b, an annular holding surface 13p that is a circumferential surface facing the distal end side is formed at the position where the inner cavity of the distal end part 12a and the inner cavity of the proximal end part 12b communicate with each other. The proximal end part of the coil spring 40 is fixed to the holding surface 13p. The dimension of the holding portion 13 in the direction along the longitudinal axis C1 is set to a dimension that allows the coil spring 40 to be accommodated in the holding portion 13 in a state in which the clip unit 20 is in contact with the distal end member 12.

The clip unit 20 is detachably connected to the distal end part of the sheath 10. In the present embodiment, since the distal end member 12 is provided at the distal end part of the sheath 10, the clip unit 20 is detachably connected to the distal end member 12.

The clip unit 20 includes a clip body 60, a holding tube 70, and a second rotation preventing part 80.

The clip body 60 is elastically deformable and is connected to the operation member 30. The clip body 60 has a first arm part 61 and a second arm part 62 arranged to face each other. The first arm part 61 and the second arm part 62 are formed so as to extend from the proximal end side toward the distal end side. In addition, the first arm part 61 and the second arm part 62 are arranged such that the distal end part of the first arm part 61 and the distal end part of the second arm part 62 are separated from each other.

The clip body 60 further includes a coupling part 63. The coupling part 63 is disposed between the proximal end part of the first arm part 61 and the proximal end part of the second arm part 62, and connects the first arm part 61 and the second arm part 62 to each other. The proximal end part of the first arm part 61 and the proximal end part of the second arm part 62 linearly extend from the coupling part 63 toward the distal side along the longitudinal axis C1 so as to be parallel to each other. The distal end part of the first arm part 61 and the distal end part of the second arm part 62 extend so as to be separated from each other from the respective proximal end parts toward the distal end side.

A claw portion 61a extending toward the second arm part 62 is formed at the distal end of the first arm part 61. A claw portion 62a extending toward the first arm part 61 is formed at the distal end of the second arm part 62.

As described above, in the natural state in which no external force is applied, the distal end part of the first arm part 61 and the distal end part of the second arm part 62 are separated from each other. By applying an external force to the first arm part 61 and the second arm part 62, the clip body 60 is elastically deformed, and the distal end part of the first arm part 61 and the distal end part of the second arm part 62 can be brought close to each other.

Figure 3:
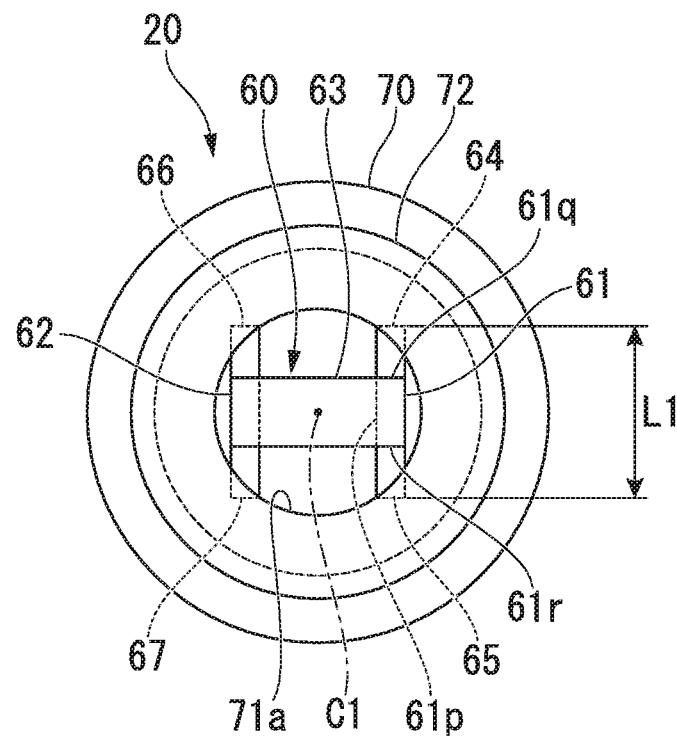
FIG. 3 is a view showing a clip unit of the endoscopic treatment tool as viewed from a direction A2 in FIG. 2.

FIG. 3 is a view showing the clip unit 20 as seen from the direction A2 in FIG. 2. In FIG. 3, for ease of explanation, components not necessary for explanation are appropriately omitted. As shown in FIGS. 2 and 3, a first protrusion 64 and a second protrusion 65 are formed on the proximal end part of the first arm part 61. The proximal end part of the first arm part 61 has a substantially rectangular cross section as seen from a direction along the longitudinal axis C1. The first protrusion 64 and the second protrusion 65 are respectively provided on a side surface 61q and a side surface 61r extending from the opposing surface 61p facing the proximal end part of the second arm part 62 at the proximal end part of the first arm part 61, and are formed so as to protrude from the side surface 61q and the side surface 61r in parallel to the opposing surface 61p.

The first protrusion 64 has a distal end surface 64p and a proximal end surface 64q. The distal end surface 64p is formed so as to have a positional relationship perpendicular to the facing surface 61p and is formed to be orthogonal to the side surface 61q. The proximal end surface 64q is formed so as to be in a positional relationship perpendicular to the opposing surface 61p and is inclined so as to be separated from the side surface 61q from the proximal end side toward the distal end side.

The second protrusion 65 is formed to be symmetrical with respect to the first protrusion 64 and a plane perpendicular to the facing surface 61p and overlapping the longitudinal axis C1. The second protrusion 65 has a distal end surface 65p corresponding to the distal end surface 64p of the first protrusion 64 and a proximal end surface 65q corresponding to the proximal end surface 64q of the first protrusion 64.

Similarly to the first arm part 61, a first protruding portion 66 and a second protruding portion 67 are formed at the proximal end part of the second arm part 62. The first protrusion 64 and the second protrusion 65 of the first arm part 61, and the first protrusion 66 and the second protrusion 67 of the second arm part 62 are arranged at the same position in the direction along the longitudinal axis C1.

The clip body 60 is made of, for example, a material such as a cobalt chrome alloy, titanium, stainless steel or the like.

The holding tube 70 is formed in a cylindrical shape. A proximal end part 60*b* (the proximal end part of the first arm part 61, the proximal end part of the second arm part 62, and the coupling part 63) of the clip body 60 is disposed inside the holding tube 70. The inner diameter of the holding tube 70 is set to be larger than the largest dimension in the cross section orthogonal to the longitudinal axis C1 at the proximal end part 60*b* of the clip body 60. The inner diameter of the holding tube 70 is set to be smaller than the distance at which the first arm part 61 and the second arm part 62 are most distant from each other when the clip body 60 is in the natural state.

When the clip body 60 is moved to the proximal end side inside the holding tube 70 by operating the operation member 30, the first arm part 61 and the second arm part 62, which are separated from each other, are pushed in the direction to approach each other by the inner peripheral surface of the holding tube 70. As a result, the clip body 60 is elastically deformed such that the first arm part 61 and the second arm part 62 approach each other, and the target tissue T can be grasped by the first arm part 61 and the second arm part 62.

A latching part 71 is formed at the proximal end part of the holding tube 70. The latching part 71 is formed so as to protrude inward in the radial direction from the inner peripheral surface of the holding tube 70 along a plane orthogonal to the longitudinal axis C1 and is provided over the entire circumference. As a result, a bore having an inner diameter smaller than the inner diameter of the other portion of the holding tube 70 is formed in the latching part 71.

The inner diameter of the latching part 71 is set to a size allowing insertion of the distal end side of the operation member 30. The inner diameter of the latching part 71 is set to such a size that the proximal end part 60*b* can be inserted by elastically deforming the proximal end part 60*b* of the clip body 60.

As shown in FIG. 3, the inner diameter of the latching part 71 is set to be larger than the length L1 from the protruding end of the first protrusion 64 of the first arm part 61 to the protruding end of the second protruding portion 65 in the plane orthogonal to the longitudinal axis C1, in the case where the clip body 60 is in the natural state. However, in the orientation of the clip body 60 in the natural state, the projecting end of the first protrusion 64 and the protruding end of the second protruding portion 65 are set to be overlap the inner peripheral edge 71*a* of the latching part 71 when viewed from the direction along the longitudinal axis C1. The latching part 71 also has a dimensional relationship with respect to the second arm part 62 similar to the first arm part 61. Therefore, when the clip body 60 is in the natural state, the proximal end part 60*b* of the clip body 60 cannot pass through the inner cavity of the latching part 71. However, when the clip body 60 is elastically deformed and the proximal end part of the first arm part 61 and the proximal end part of the second arm part 62 are close to each other, the proximal end part 60*b* of the clip body 60 is engaged with the latching part 71 through the inner cavity.

A stepped portion 72 is formed at the proximal end part of the holding tube 70. The stepped portion 72 is formed so as to be recessed radially inward from the outer peripheral surface of the holding tube 70, and is provided over the entire circumference. Therefore, the outer diameter of the stepped portion 72 is set to be smaller than the outer diameter of the other portion of the holding tube 70. The outer diameter of the stepped portion 72 is set to be slightly smaller than the inner diameter of the holding portion 13 of the distal end member 12. Accordingly, the stepped portion 72 can be fitted into the holding portion 13.

The holding tube 70 is made of a metal material such as stainless steel, a titanium alloy (Ti-6Al-4V or the like), a cobalt chromium alloy or the like, or a resin material with a high rigidity having moderate elasticity such as polyphthalamide (PPA), polyamide (PA), or the like.

The second rotation preventing part 80 is configured such that it is possible to prevent the clip body 60 from rotating relative to the holding tube 70 about the longitudinal axis C1 in the open state when the first arm part 61 and the second arm part 62 of the clip body 60 are separated from each other.

In the present embodiment, the second rotation preventing part 80 has a first notch portion 81 and a second notch portion 82 provided in the peripheral edge part 73 on the distal end side of the holding tube 70. The first notch portion 81 and the second notch portion 82 are disposed at positions opposed to each other across the longitudinal axis C1. The first notch portion 81 and the second notch portion 82 respectively extend from the distal end surface of the holding tube 70 toward the proximal end side, and are formed so as to penetrate the holding tube 70 from the inner peripheral surface to the outer peripheral surface.

The first arm part 61 of the clip body 60 is arranged to pass through the inside of the first notch portion 81. Further, the second arm part 62 is disposed so as to pass through the inside of the second notch portion 82. Therefore, the dimension between the inner surfaces facing the circumferential direction of the holding tube 70 in the first notch portion 81 is set slightly larger than the outer dimension of the first arm part 61 in the cross section orthogonal to the longitudinal axis C1. Similarly, the dimension between the inner surfaces facing the circumferential direction of the holding tube 70 in the second notch portion 82 is set slightly larger than the outer dimension of the second arm part 62 in the cross section orthogonal to the longitudinal axis C1.

For example, when the clip body 60 tries to rotate about the longitudinal axis C1, the first arm part 61 contacts the inner surface of the first notch portion 81, and the second arm part 62 contacts the second notch portion 82 according to the above-described configuration. Therefore, as the clip body 60 rotates, the holding tube 70 rotates. Alternatively, when the holding tube 70 does not move, the rotation of the clip body 60 is stopped by the holding tube 70. That is, the clip body 60 is prevented from relatively rotating around the longitudinal axis C1 with respect to the holding tube 70. Further, according to the above-described configuration, even when the first arm part 61 and the second arm part 62 of the clip body 60 are the most distant from each other, the second rotation preventing part 80 can prevent the clip body 60 from rotating around the longitudinal axis C1 with respect to the holding tube 70.

The operation member 30 is inserted into the sheath 10 so as to be able to advance and retreat, and is connected to the clip unit 20. The operation member 30 has an operation wire 31 and a connecting member 32.

The operation wire 31 is formed to extend along the longitudinal axis C1 and inserted into the sheath 10 so as to be able to advance and retreat. The operation wire 31 is formed of, for example, a metal single wire or a stranded wire.

The connecting member 32 is fixed to the distal end part of the operation wire 31. The connecting member 32 is a portion to be connected to the coupling part 63 of the clip body 60 in the operation member 30. The connecting member 32 includes a main body portion 33 and a hook portion 34. The main body portion 33 is formed in a flat plate shape extending along the longitudinal axis C1. The distal end part of the operation wire 31 is fixed to the proximal end part of the main body portion 33 by welding or the like.

The hook portion 34 is provided at the distal end part of the main body portion 33. The hook portion 34 has a shape engageable with the coupling part 63 of the clip body 60. Specifically, in the present embodiment, the hook portion 34 is formed to extend in a substantially J-shape from the distal end part of the main body portion 33 to the distal end side. That is, the hook portion 34 has a straight portion linearly extending from the distal end part of the main body portion 33 to the distal end side along the longitudinal axis C1, and a curved portion extending in a circular arc shape from the distal end part of the straight portion to the distal end part of the main body portion 33.

Figure 4:
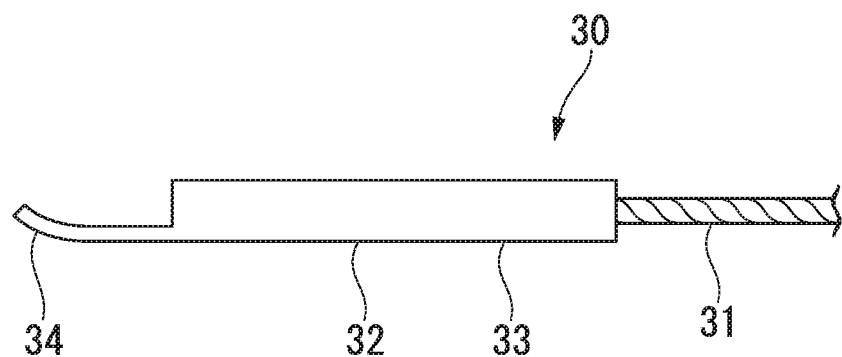
FIG. 4 is a view showing a state in which a hook portion of a connecting member of the endoscopic treatment instrument is deformed.

The hook portion 34 is formed of a member that can be elastically deformed or plastically deformed in a substantially straight line when a tensile force of a predetermined magnitude is applied in a direction along the longitudinal axis C1. FIG. 4 is a view showing a state in which the hook portion 34 of the connecting member 32 is deformed. As shown in FIG. 4, when the hook portion 34 is deformed substantially linearly, the engagement between the hook portion 34 and the coupling part 63 of the clip body 60 is released.

The coil spring (biasing member) 40 is disposed between the distal end part of the sheath 10 and the clip unit 20. Further, the coil spring 40 biases the holding tube 70 so as to separate from the distal end part of the sheath 10.

In the present embodiment, the coil spring 40 is disposed between the distal end part of the sheath 10 and the holding tube 70. The coil spring 40 is formed by spirally winding the strand along the longitudinal axis C1. That is, the coil spring 40 is formed by winding a strand so that adjacent strands are separated from each other. The coil spring 40 can be accommodated in the holding portion 13 of the distal end member 12 in a state compressed along the longitudinal axis C1. Therefore, the outer diameter of the coil spring 40 is set to be smaller than the inner diameter of the holding portion 13. The proximal end part of the coil spring 40 is fixed to the holding surface 13p of the holding portion 13. Therefore, the inner diameter of the coil spring 40 is set to be larger than the inner diameter of the proximal end part 12b of the distal end member 12. As a result, the internal space of the coil spring 40 communicates with the internal cavity of the proximal end part 12b of the distal end member 12 and the internal cavity of the coil sheath 11.

The distal end part of the coil spring 40 is in contact with a contact surface 70s provided at the proximal end part of the holding tube 70. The contact surface 70s is an annular surface facing the proximal end side of the latching part 71 of the holding tube 70. Since the coil spring 40 contacts the contact surface 70s, the inner diameter of the coil spring 40 is set to be larger than the inner diameter of the latching part 71. As a result, the internal space of the coil spring 40 communicates with the internal cavity of the holding tube 70 via the internal cavity of the latching part 71. The outer diameter of the coil spring 40 is set to be smaller than the outer diameter of the stepped portion 72. The operation member 30 passes through the inner space of the coil spring 40 from the inner cavity of the proximal end part 12b of the distal end member 12 and is inserted into the inner cavity of the holding tube 70.

The dimension of the coil spring 40 in the direction along the longitudinal axis C1 in the natural state in which no external force is applied to the coil spring 40 is set to be larger than the dimension of the holding portion 13 in the direction along the longitudinal axis C1. Therefore, when the coil spring 40 is in the natural state, the proximal end part of the holding tube 70 is separated from the distal end part 12a of the distal end member 12 in the direction along the longitudinal axis C1. In this state, the distal end part of the coil spring 40 is merely in contact with the contact surface 70s of the holding tube 70, so that the holding tube 70 can rotate relative to the distal end member 12. Further, for example, when an external force larger than the restoring force (biasing force) of the coil spring 40 is applied to the holding tube 70 in the direction along the longitudinal axis C1 toward the proximal end side, the coil spring 40 is compressed and the holding tube 70 of the stepped portion 72 can be fitted into the holding portion 13 of the distal end member 12.

The restoring force of the coil spring 40 is set to be smaller than the force required for the clip body 60 to move toward the proximal end side in the holding tube 70 to bring the first arm part 61 and the second arm part 62 close to each other. Therefore, when an external force is applied to the clip body 60 or when the clip body 60 is pulled inside the holding tube 70 by the operation member 30, the coil spring 40 is first compressed before the clip body 60 moves to the proximal end side in the holding tube 70 and the first arm part 61 and the second arm part 62 come close to each other.

The coil spring 40 is made of, for example, a material such as a cobalt chrome alloy, titanium, stainless steel or the like.

The first rotation preventing part 50 is configured to be able to prevent relative rotation of the clip unit 20 around the longitudinal axis C1 with respect to the distal end part of the sheath 10. When the proximal end part of the holding tube 70 comes into contact with the distal end part of the sheath 10 against the biasing force of the coil spring 40, the first rotation preventing part 50 prevents relative rotation of the clip unit 20.

Figure 5:
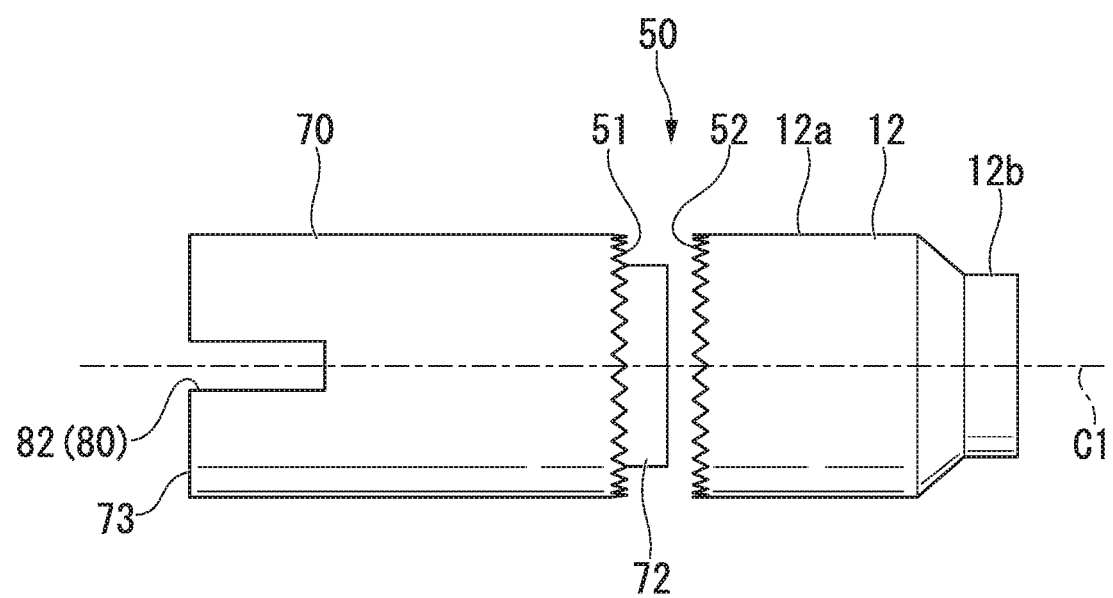
FIG. 5 is a view schematically showing a first rotation preventing part of the endoscopic treatment tool.

FIG. 5 is a diagram schematically showing the first rotation preventing part 50. In FIG. 5, in order to facilitate the explanation, configurations other than the distal end member 12 and the holding tube 70 are omitted. As shown in FIG. 5, in the present embodiment, the first rotation preventing part 50 includes a first engaging portion 51 of a concave-convex shape and a second engaging portion 52 engageable with the first engaging portion 51. The first engaging portion 51 is formed on the proximal end surface 70t of the holding tube 70. The proximal end surface 70t is an annular surface facing the proximal end side in the stepped portion 72 and is arranged so as to surround the contact surface 70s when viewed from the direction along the longitudinal axis C1. In addition, the second engaging portion 52 is formed on the distal end surface (the distal end surface of the sheath 10) of the distal end member 12. Each of the first engaging portion 51 and the second engaging portion 52 has has a plurality of protruding portions having a same shape with each other and protruding in a direction along the longitudinal axis C1, and a plurality of groove portions having a same shape with each other and recessed in the direction along the longitudinal axis C1. The plurality of protrusions and the plurality of groove portions are alternately arranged. In addition, the protruding portion and the groove portion are formed so as to be engaged with each other.

The proximal end surface 70t of the holding tube 70 contacts the distal end surface of the distal end member 12 against the biasing force of the coil spring 40, whereby the first engaging portion 51 engages with the second engaging portion 52. More specifically, the first engaging portion 51 engages with the second engaging portion 52. In this state, since the first engaging portion 51 and the second engaging portion 52 are engaged with each other, relative rotation of the holding tube 70 with respect to the distal end member 12 around the longitudinal axis C1 is prevented. That is, relative rotation of the clip unit 20 around the longitudinal axis C1 with respect to the distal end part of the sheath 10 is prevented.

In the first engaging portion 51 and the second engaging portion 52, a plurality of projecting portions and a plurality of groove portions may be arranged so that the first engaging portion 51 and the second engaging portion 52 engage each other, for example, each time they are rotated by about 10 degrees about the longitudinal axis C1. This makes it possible to adjust the rotation angle of the holding tube 70 around the longitudinal axis C1 with respect to the distal end member 12 when the first engaging portion 51 engages with the second engaging portion 52 in more steps.

Further, in the present embodiment, a stepped portion 72 to be fitted into the holding portion 13 of the distal end member 12 is provided in the holding tube 70. Therefore, when the proximal end surface 70t of the holding tube 70 contacts the distal end surface of the distal end member 12, the holding tube 70 does not deviate from the distal end member 12 in the direction orthogonal to the longitudinal axis C1, and the first engaging portion 51 can engage with the second engaging portion 52.

As shown in FIG. 1, the endoscopic treatment instrument 1 further includes a mantle tube 90 and an operation section 100.

The mantle tube 90 has flexibility and is formed in a cylindrical shape extending along the longitudinal axis C1. The sheath 10 is inserted into the mantle tube 90 so as to advance and retract. The mantle tube 90 can be formed of a fluororesin such as PTFE (polytetrafluoroethylene) or a resin material such as HDPE (high density polyethylene).

The operation section 100 is provided on the proximal end side of the sheath 10. The operation section 100 includes an operation section main body 101 and a slider 102.

The operation section main body 101 is formed in a rod shape extending along the longitudinal axis C1. The operation section main body 101 is attached to the proximal end part of the coil sheath 11 so as to be rotatable around the longitudinal axis C1. For example, a latching part protruding radially outwardly is provided at a proximal end part of the coil sheath 11, and a distal end part of the operation section main body 101 is provided with an annular engaging groove which engages with the latching part. With such a configuration, the operation section main body 101 can rotate around the longitudinal axis C1 with respect to the coil sheath 11. A finger hooking portion 101a is provided at the proximal end part of the operation section main body 101. A slit 101b extending along the longitudinal axis C1 is formed in the operation section main body 101.

The slider 102 is formed in a cylindrical shape and attached to the operation section main body 101 so as to be slidable in a direction along the longitudinal axis C1. A proximal end part of the operation wire 31 is fixed to the slider 102. Therefore, by advancing and retreating the slider 102 in the direction along the longitudinal axis C1, the operation wire 31 can be advanced and retracted. Further, the slider 102 is engaged with the slit 101b. As a result, the movement range of the slider 102 with respect to the operation section main body 101 is limited.

Figure 6:
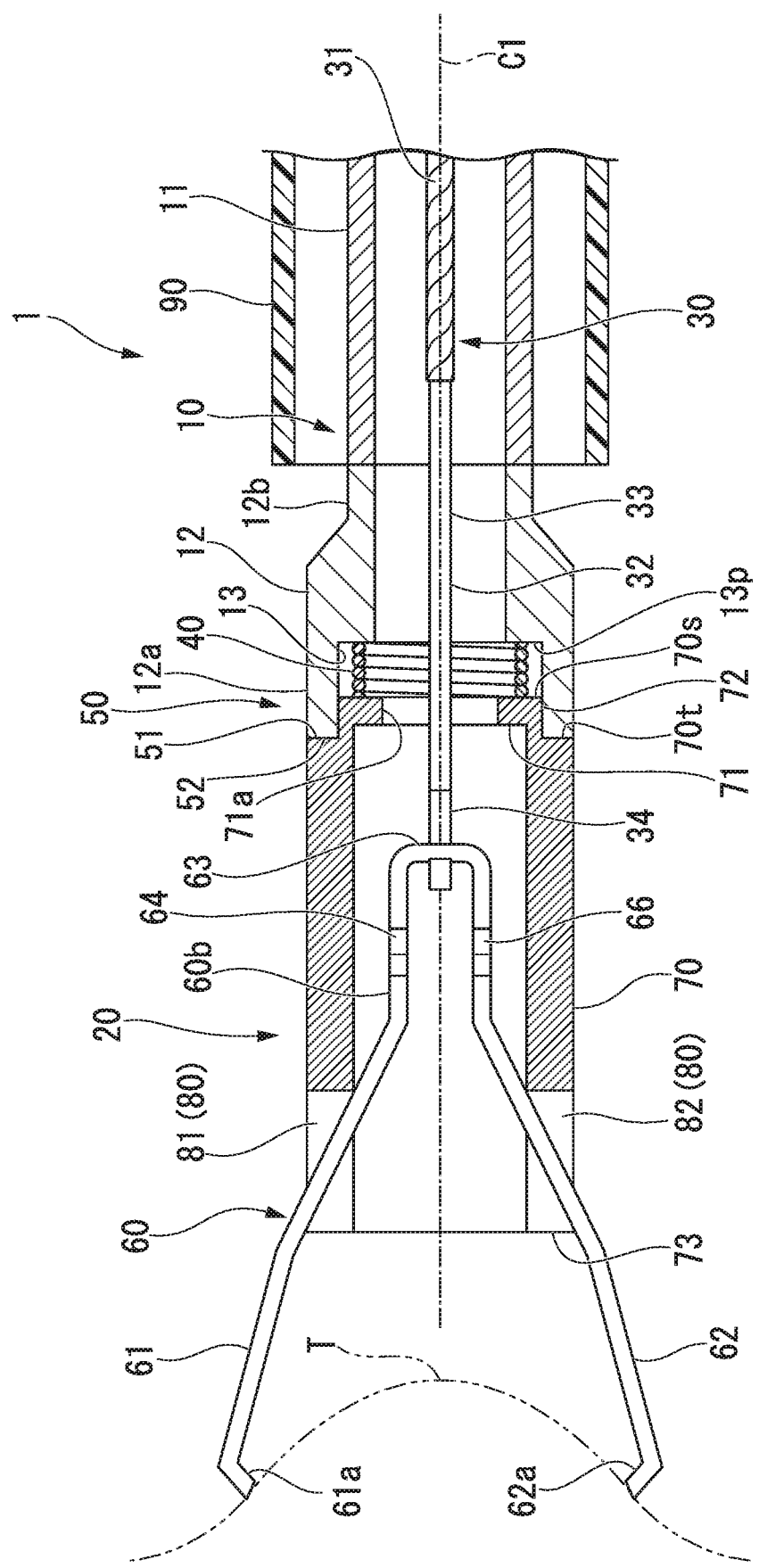
FIG. 6 is a diagram showing the operation of the endoscopic treatment instrument.
Figure 7:
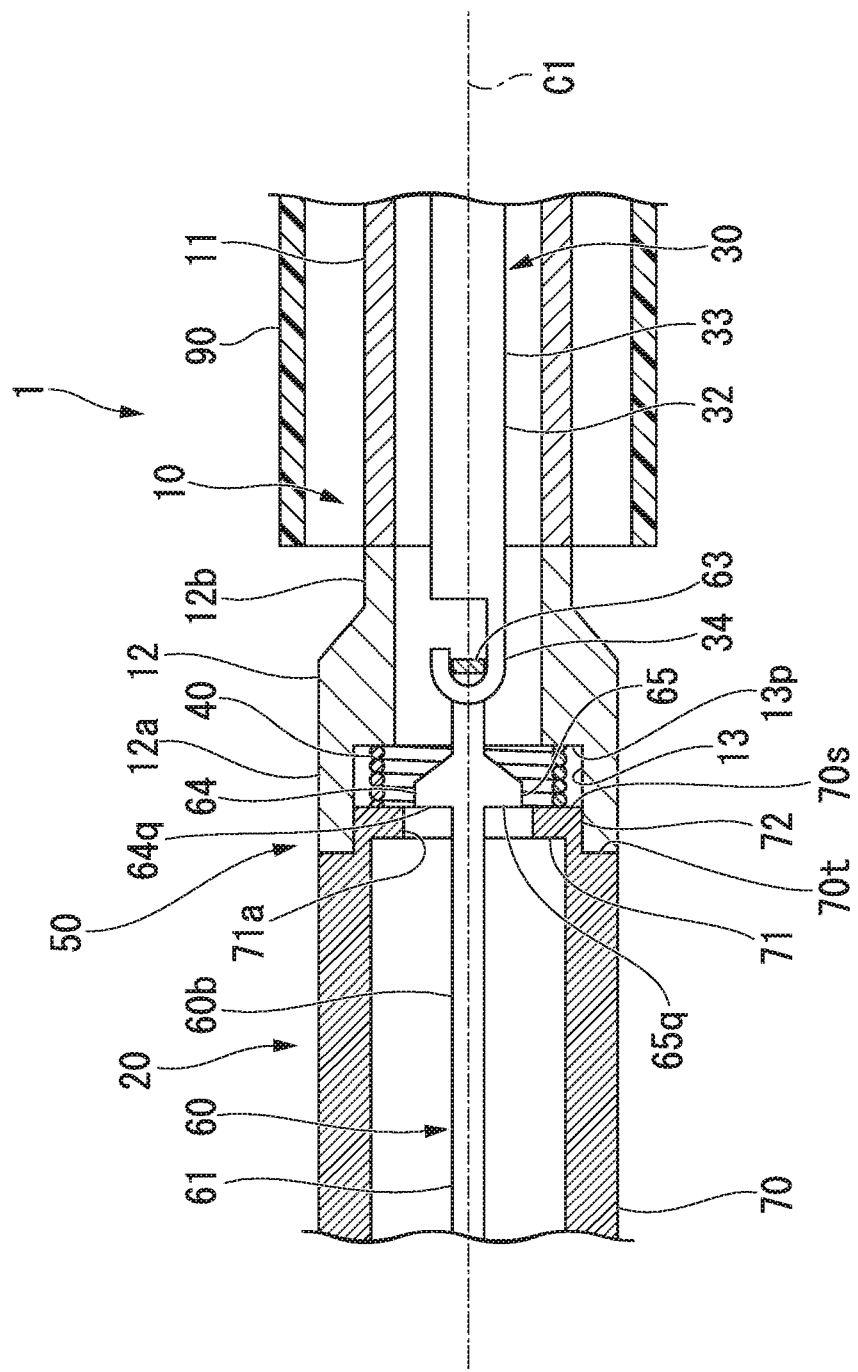
FIG. 7 is a diagram showing the operation of the endoscopic treatment instrument.
Figure 8:
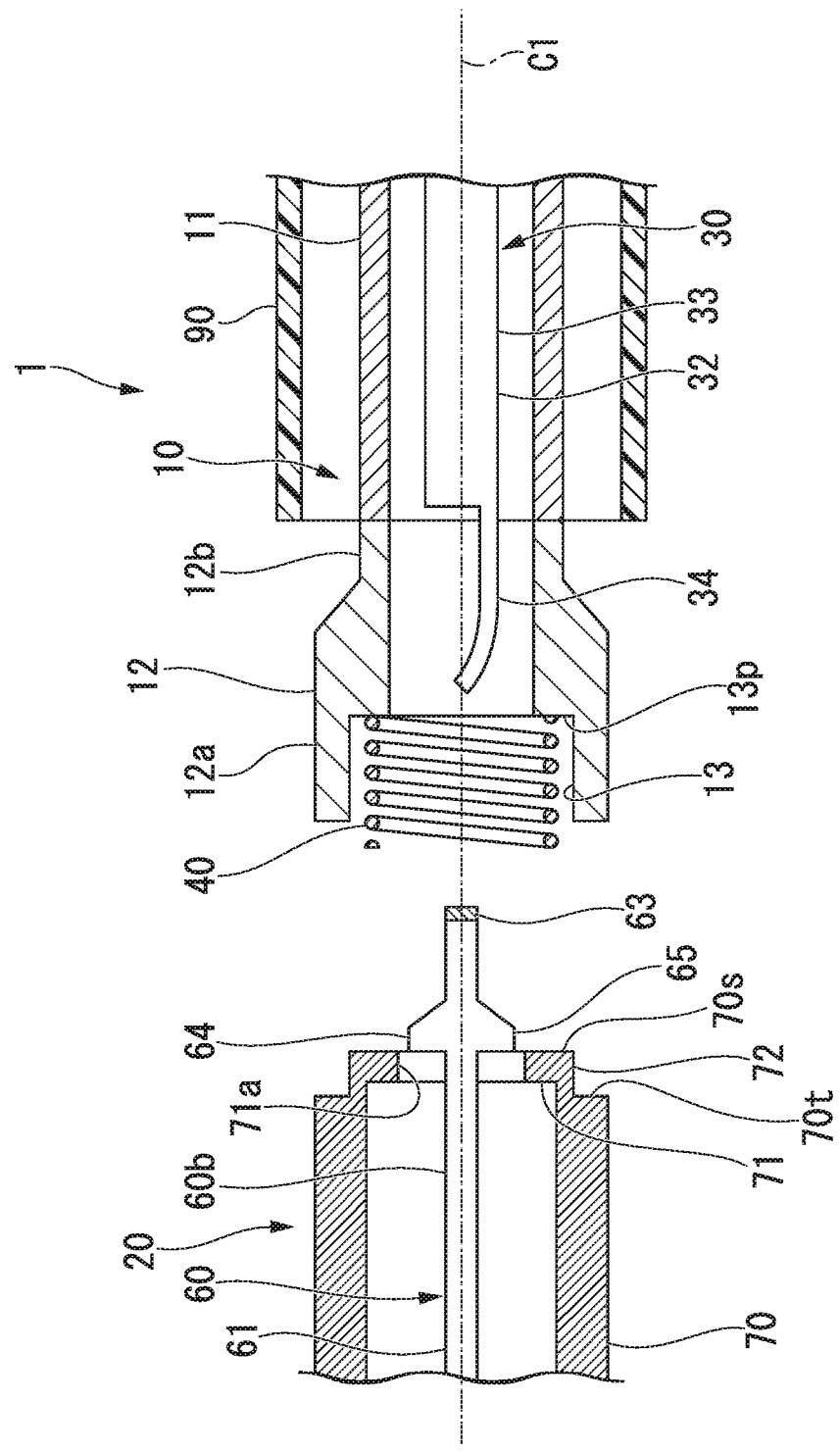
FIG. 8 is a view showing the operation of the endoscopic treatment instrument.

Next, the operation of the endoscopic treatment instrument 1 in the procedure of ligating the target tissue T will be described. FIGS. 6 to 8 are diagrams showing the operation of the endoscopic treatment instrument 1.

First, the surgeon inserts the insertion portion of the endoscope (not shown) into the body of patient. Then, the endoscopic treatment instrument 1 is inserted into the channel of the endoscope. At this time, the clip unit 20 is drawn into the mantle tube 90 so that the clip unit 20 is disposed inside the mantle tube 90. The mantle tube 90 projects from the distal end of the channel. By retracting the mantle tube 90 relative to the sheath 10, the clip unit 20 protrudes from the distal end of the mantle tube 90 as shown in FIG. 1. As a result, the first arm part 61 and the second arm part 62 of the clip body 60 are in a state of being most separated from each other.

Subsequently, the surgeon rotates the operation section 100 around the longitudinal axis C1 so that the first arm part 61 and the second arm part 62 face the target tissue T in an appropriate direction. When the operation section 100 rotates, the clip body 60 rotates about the longitudinal axis C1 via the operation member 30. At this time, since the holding tube 70 is separated from the distal end member 12 by the coil spring 40, the holding tube 70 rotates together with the clip body 60 by the action of the second rotation preventing part 80.

In a state in which the first arm part 61 and the second arm part 62 are oriented in an appropriate direction with respect to the target tissue T, the surgeon pushes the operation section 100 and presses the clip body 60 against the target tissue T. At this time, as shown in FIG. 6, the coil spring 40 is compressed by the reaction force received from the target tissue T, and the stepped portion 72 of the holding tube 70 is fitted into the holding portion 13 of the distal end member 12. Along with this, the proximal end surface 70t of the holding tube 70 contacts the distal end surface of the distal end member 12, whereby the first engaging portion 51 engages with the second engaging portion 52. This prevents the holding tube 70 from rotating relative to the distal end member 12 about the longitudinal axis C1. The clip body 60 is prevented from relative rotation around the longitudinal axis C1 with respect to the holding tube 70 by the second rotation preventing part 80. As a result, the clip body 60 is prevented from relatively rotating around the longitudinal axis C1. Therefore, even if the clip body 60 receives a reaction force from the target tissue T, the clip body 60 does not rotate around the longitudinal axis C1.

In this state, the operator pulls the slider 102 toward the proximal end side, and as shown in FIG. 7, the operation member 30 is pulled until the first protrusion 64 and the second protrusion 65 of the first arm part 61, and the first protrusion 66 and the second protrusion 67 of the second arm part 62 of the clip body 60 pass through the inner cavity of the latching part 71 of the holding tube 70 and move to the outside of the holding tube 70.

At this time, since the proximal end surface 64q of the first protrusion 64 and the proximal end surface 65q of the second protrusion 65 are inclined as described above in the first arm part 61, while the proximal end surface 64q and the proximal end surface 65q contact the inner peripheral edge 71a of the latching part 71, the proximal end part of the first arm part 61 moves so as to be close to the proximal end part of the second arm part 62 by elastic deformation. Similarly, the proximal end part of the second arm part 62 moves so as to be close to the proximal end part of the first arm part 61 by elastic deformation. When the proximal end part of the first arm part 61 and the proximal end part of the second arm part 62 are brought to a position where the dimension of the inner cavity of the latching part 71 is larger than the length L1 from the protruding end of the first protruding portion 64 to the protruding end of the second protruding portion 65, the first protruding portion 64 and the second protruding portion 65 of the first arm part 61, and the first protruding portion 66 and the second protruding portion 67 of the second arm part 62 passes through the inner cavity of the latching part 71 of the holding tube 70.

After the first protrusion 64 and the second protrusion 65 of the first arm part 61, and the first protrusion 66 and the second protrusion 67 of the second arm part 62 pass through the inner cavity of the latching part 71 of the holding tube 70, when the clip body 60 is pulled toward the distal end side by an external force or the like, the distal end surface 64p of the first protruding portion 64, the distal end surface 65p of the second protruding portion 65, the distal end surface (not shown) of the first protruding portion 66, and the distal end surface (not shown) of the second protrusion 67 come into contact with the contact surface 70s of the latching part 71. Thereby, the clip body 60 is prevented from moving to the distal end side.

As the clip body 60 moves inside the holding tube 70 to the proximal end side, the first arm part 61 and the second arm part 62 come close to each other. As a result, the first arm part 61 and the second arm part 62 sandwich the target tissue T.

In a state in which the first arm part 61 and the second arm part 62 sandwich the target tissue T, the clip body 60 cannot be elastically deformed such that the first arm part 61 and the second arm part 62 are further closer to each other. Therefore, even if the operator further pulls the slider 102 toward the proximal end side, the first arm part 61 and the second arm part 62 come into contact with the holding tube 70, and the clip body 60 cannot move the inside of the holding tube 70 to the proximal end. Instead, the tension applied to the operation member 30 increases. When the tension exceeds the predetermined magnitude, the hook portion 34 of the connecting member 32 of the operation member 30 is deformed so as to extend substantially linearly (see FIG. 4). As a result, the hook portion 34 is disengaged from the clip body 60, and the holding tube 70 is separated from the distal end member 12 by the biasing force of the coil spring 40.

After the clip unit 20 is thus separated from the sheath 10 as shown in FIG. 8, the sheath 10 and the operation member 30 are accommodated in the mantle tube 90. The endoscope treatment tool 1 is extracted from the endoscope channel. The insertion part of the endoscope is removed from inside the body of patient. This concludes a series of procedures.

The endoscopic treatment instrument 1 according to the present embodiment includes: a sheath 10 having a long axis C1 and formed in an elongated shape; a clip unit 20 detachably connected to a distal end part of the sheath 10; an operation member 30 inserted into the inside of the sheath 10 and connected to the clip unit 20; a coil spring 40 which is an biasing member disposed between the distal end part of the sheath 10 and the clip unit 20; and a first rotation preventing part 50 configured to be able to prevent the clip unit 20 from relatively rotating around the longitudinal axis C1 with respect to the distal end part of the sheath 10. The clip unit 20 includes: a clip body 60 having a first arm part 61 and a second arm part 62 which are arranged to face each other and whose distal ends are spaced apart from each other, and which is connected to the operation member 30 and is elastically deformable; a holding tube 70 formed in a cylindrical shape and having proximal end part 60b of the clip body 60 inside thereof; and a second rotation preventing part 80 configured to be able to prevent the clip body 60 from relatively rotating around the longitudinal axis C1 in an open state in which the first arm part 61 and the second arm part 62 are separated from each other. The coil spring 40 biases the holding tube 70 so as to be separated from the distal end part of the sheath 10. When the proximal end part of the holding tube 70 comes into contact with the distal end part of the sheath 10 against the biasing force of the coil spring 40, the first rotation preventing part 50 prevents relative rotation of the clip unit 20.

According to the configuration described above, in a state in which the clip body 60 is not pressed against the target tissue T, the coil spring 40 biases the holding tube 70 to separate from the distal end part of the sheath 10, so that the clip body 60 and the holding tube 70 can be rotated relative to the sheath 10 about the longitudinal axis C1. On the other hand, when the clip body 60 is pressed against the target tissue T, the proximal end part of the holding tube 70 contacts the distal end part of the sheath 10, and the first rotation preventing part 50 prevents relative rotation of the clip unit 20. Thereby, it is possible to prevent the clip body 60 and the holding tube 70 from relatively rotating with respect to the sheath 10 around the longitudinal axis C1.

In the present embodiment, when a tensile force of a predetermined magnitude is applied in the direction along the longitudinal axis C1, the hook portion 34 of the connecting member 32 elastically deforms or plastically deforms substantially linearly. However, the hook portion 34 may not be deformed substantially linearly but may be configured so that the curved portion is broken halfway. Even with such a configuration, the engagement between the hook portion 34 and the coupling part 63 of the clip body 60 can be released.

In the above description, the biasing member is the coil spring 40, but it is not limited thereto. The biasing member may be other known springs or elastic bodies.

In the above description, the second rotation preventing part 80 has the first notch portion 81 and the second notch portion 82, but it is not limited thereto. The second rotation preventing part 80 is not limited as long as the second rotation preventing part 80 is configured so as to be able to prevent the clip body 60 from rotating relatively to the holding tube 70 about the longitudinal axis C1 in a state in which the first arm part 61 and the second arm part 62 of the clip body 60 are separated from each other. For example, the second rotation preventing part 80 may be formed on the peripheral edge part 73 on the distal end side of the holding tube 70, and may have an engaging portion capable of engaging with the first arm part 61 and the second arm part 62. In addition, the second rotation preventing part 80 may have a known structure for increasing the frictional force between the first arm part 61/the second arm part 62 and the peripheral part 73.

First Modification

Figure 9:
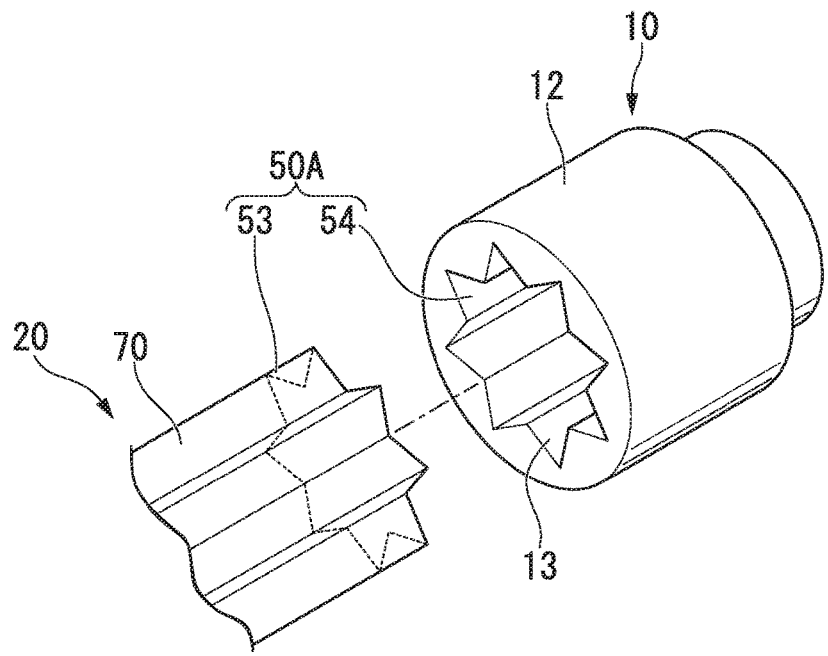
FIG. 9 is a view showing a modified example of the first rotation preventing part.

In the present embodiment, the first rotation preventing part 50 has the first engaging portion 51 and the second engaging portion 52, but it is not limited thereto. FIG. 9 is a diagram showing a modified example of the first rotation preventing part 50 according to the present embodiment. In FIG. 9, in order to facilitate the description, configurations other than the distal end member, the holding tube, and the first rotation preventing part are omitted.

The first rotation preventing part 50A of the present modification has a third engaging portion 53 having a concave-convex shape, and a fourth engaging portion 54 having a concave-convex shape and engageable with the third engaging portion 53. The third engaging portion 53 is formed on the outer peripheral surface of the holding tube 70. The fourth engaging portion 54 is formed on the inner peripheral surface of the distal end part of the sheath 10. Specifically, the fourth engaging portion 54 is formed on the inner peripheral surface of the holding portion 13 of the distal end member 12.

The third engaging portion 53 includes a plurality of protruding portions having the same shape and protruding outward in the radial direction with the longitudinal axis C1 as a center, and a plurality of groove portions having the same shape and recessed inward in the radial direction with the longitudinal axis C1 as a center. Similarly, the fourth engaging portion 54 includes a plurality of protruding portions having the same shape and protruding outward in the radial direction with the longitudinal axis C1 as the center, and a plurality of groove portions having the same shape and recessed inward in the radial direction with the longitudinal axis C1 as a center. The third engaging portion 53 and the fourth engaging portion 54 are configured such that the protruding portion of the third engaging portion 53 and the groove portion of the fourth engaging portion 54 are engaged with each other and the groove portion of the third engaging portion 53 and the protruding portion of the fourth engaging portion 54 are engaged with each other.

The proximal end part of the holding tube 70 enters the inside of the distal end part of the sheath 10, that is, the inside of the holding portion 13, whereby the third engaging portion 53 is engaged with the fourth engaging portion 54. This prevents the holding tube 70 from rotating relative to the distal end member 12 about the longitudinal axis C1. That is, relative rotation of the clip unit 20 with respect to the sheath 10 around the longitudinal axis C1 is prevented.

Further, in the third engaging portion 53 and the fourth engaging portion 54, the protruding portion and the groove portion of the third engaging portion 53 and the protruding portion and the groove portion of the fourth engaging portion 54 may be respectively arranged such that the third engaging portion 53 and the fourth engaging portion 54 are engaged with each other, for example, each time rotated by 10 degrees about the longitudinal axis C1. This makes it possible to adjust the rotation angle around the longitudinal axis C1 of the holding tube 70 with respect to the distal end member 12 when the third engaging portion 53 engages with the fourth engaging portion 54 in more steps.

Second Modification

Figure 10:
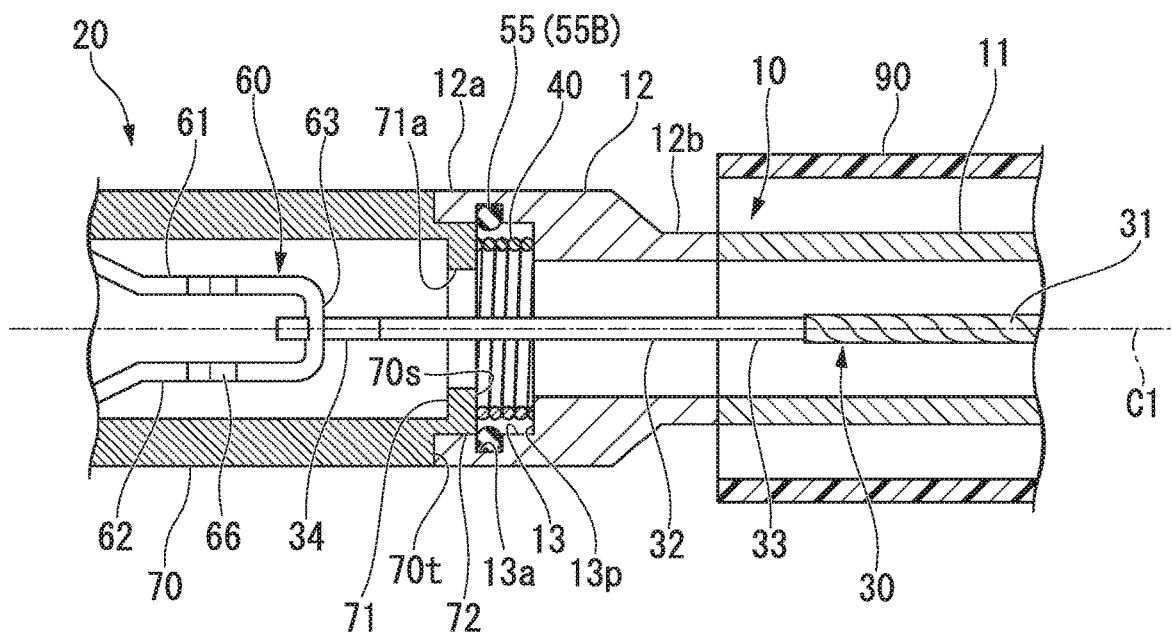
FIG. 10 is a view showing another modified example of the first rotation preventing part.

FIG. 10 is a view showing another modified example of the first rotation preventing part 50 according to the present embodiment. The first rotation preventing part 50B of this modification has a slip prevention member 55 provided on the inner peripheral surface of the distal end part of the sheath 10. Specifically, the slip prevention member 55 is provided on the inner peripheral surface of the holding portion 13 of the distal end member 12. In this modified example, the slip prevention member 55 is a known O-ring made of rubber or the like.

On the inner peripheral surface of the holding portion 13, a groove portion 13a recessed radially outward from the inner peripheral surface is formed over the entire circumference. The slip prevention member 55 is arranged in the groove portion 13a so that a part of the slip prevention member 55 protrudes radially inward from the inner peripheral surface of the holding portion 13.

As the proximal end of the holding tube 70 enters the inside of the distal end part of the sheath 10, the proximal end part of the holding tube 70 engages with the slip prevention member 55. More specifically, as the stepped portion 72 of the holding tube 70 enters the inside of the holding portion 13, the contact surface 70s of the holding tube 70 comes into contact with and engages with the slip prevention member 55. Since the slip prevention member 55 is formed of rubber or the like as described above, the frictional force generated between the slip prevention member 55 and the contact surface 70s is increased. Therefore, even if the clip body 60 receives an external force and attempts to rotate the holding tube 70, the holding tube 70 is prevented from relative rotation around the longitudinal axis C1 with respect to the distal end member 12 by this frictional force. That is, relative rotation of the clip unit 20 with respect to the sheath 10 around the longitudinal axis C1 is prevented.

In this modified example, the slip prevention member 55 is an O-ring, but it is not limited thereto. The slip prevention member 55 is not particularly limited as long as the frictional force generated between the slip prevention member 55 and the proximal end part of the holding tube 70 is increased.

Third Modified Example

Figure 11:
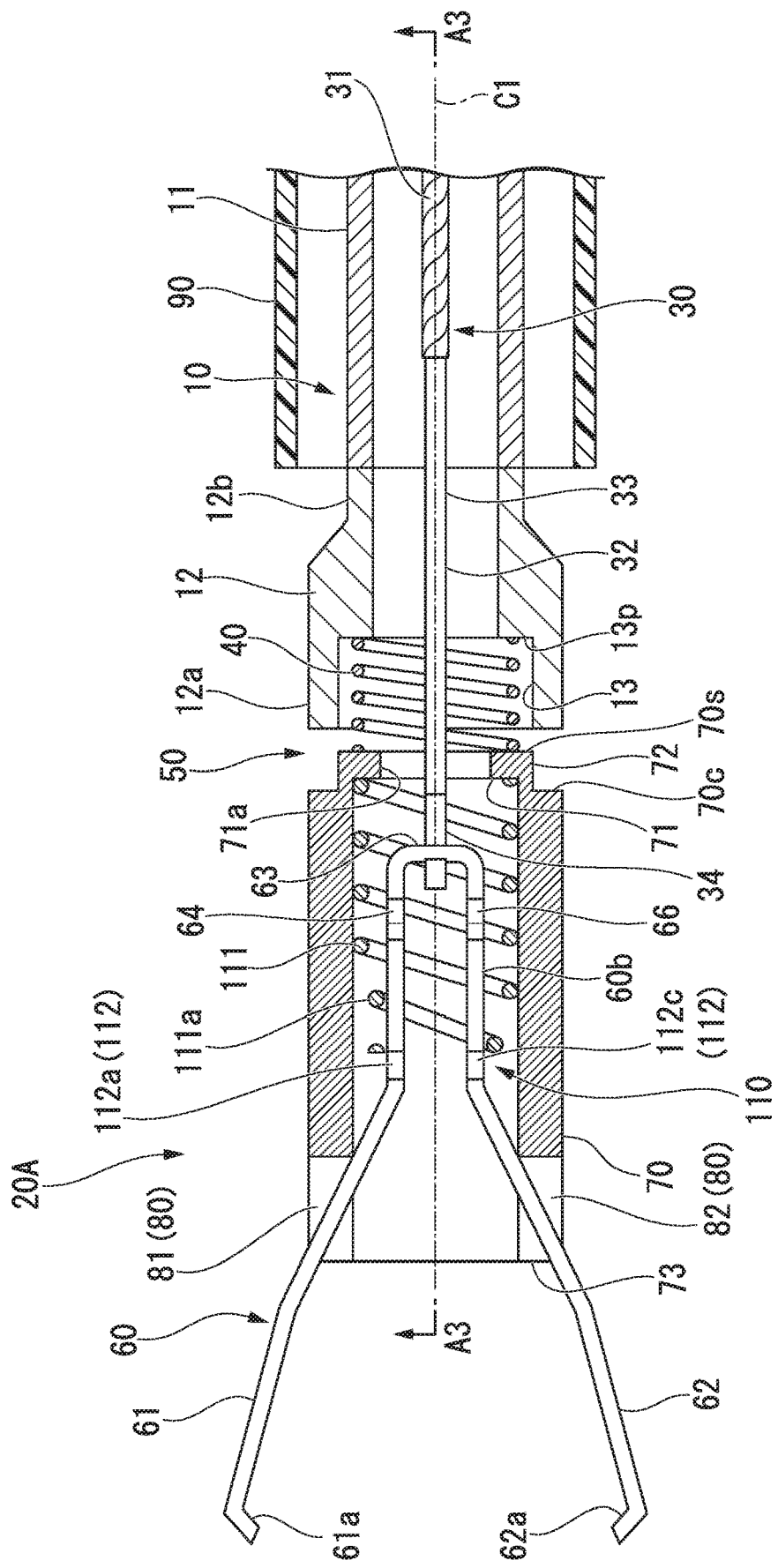
FIG. 11 is a view showing a modified example of the clip unit.
Figure 12:
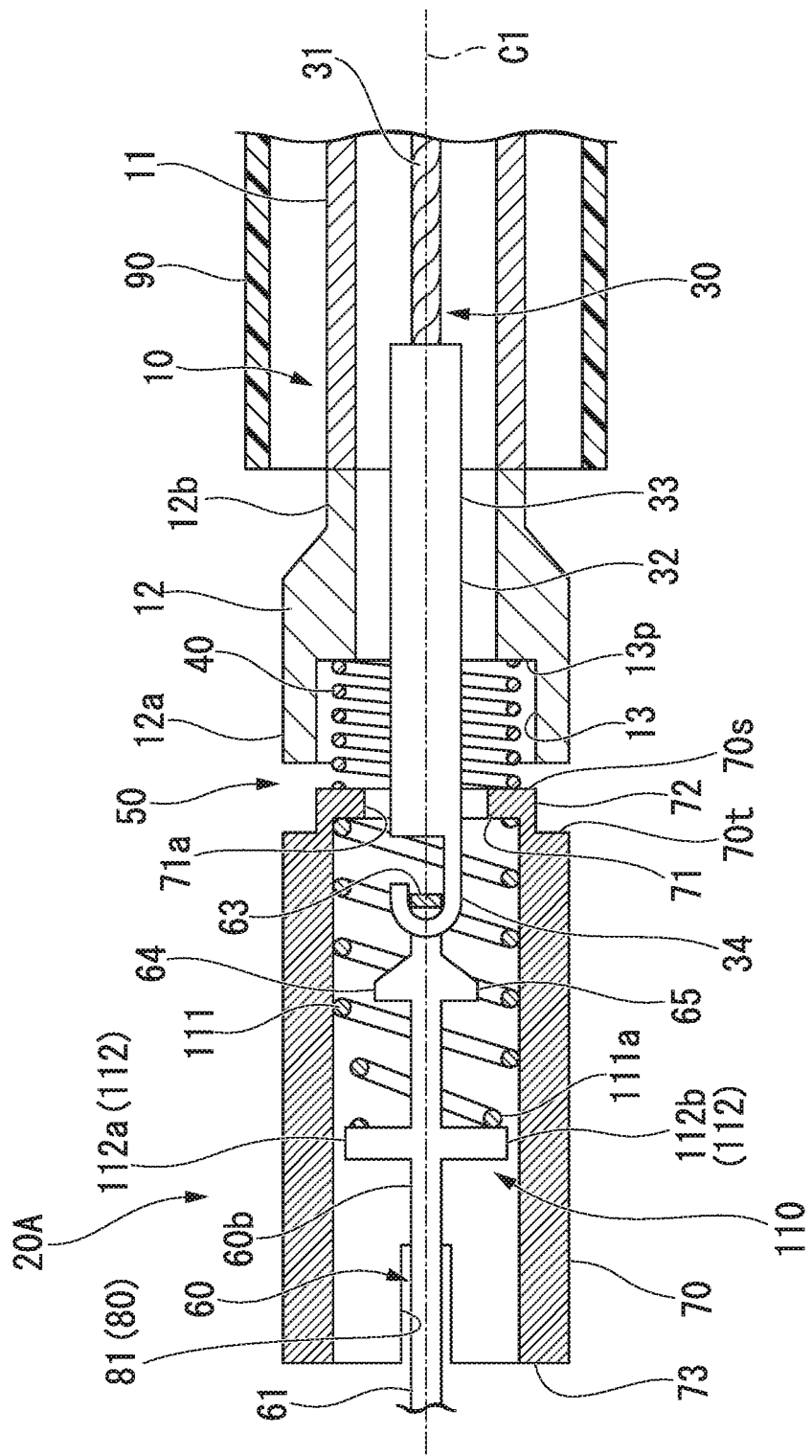
FIG. 12 is a cross-sectional view taken along the line A3-A3 in FIG. 11.

The clip unit 20 according to the above-described embodiment may further have a mechanism for facilitating grasping of the target tissue T. FIG. 11 is a view showing a modified example of the clip unit 20 according to the present embodiment. FIG. 12 is a cross-sectional view taken along line A3-A3 of FIG. 11.

The clip unit 20A of the present modification is different from the clip unit 20 in that it further includes a pushing mechanism 110. The pushing mechanism 110 has a coil spring 111 disposed inside the holding tube 70 and a contact portion 112 provided on the clip body 60.

The coil spring 111 is formed by spirally winding the strand along the longitudinal axis C1. That is, the coil spring 111 is formed by winding a strand so that adjacent strands are separated from each other. The coil spring 111 has a size that can be accommodated in the holding tube 70 in a natural state in which no external force is applied. The outer diameter of the coil spring 111 is set to be smaller than the inner diameter of the holding tube 70. The inner diameter of the coil spring 111 is set to such a dimension that the proximal end part 60b of the clip body 60 can be inserted.

An end coil portion 111a is provided at the distal end part of the coil spring 111. The end coil portion 111a is formed to have an inner diameter smaller than the other portion of the coil spring 111. The end coil portion 111a is engaged with the contact portion 112. Further, the proximal end part of the coil spring 111 is locked to the latching part 71 of the holding tube 70. It should be noted that the proximal end part of the coil spring 111 may be fixed to the latching part 71 by welding or the like.

The contact portion 112 has a first contact portion 112a, a second contact portion 112b, a third contact portion 112c, and a fourth contact portion (not shown).

The first contact portion 112a and the second contact portion 112b are provided at the proximal end part of the first arm part 61 of the clip body 60, and are disposed on more distal side than the first protruding portion 64 and the second protruding portion 65. The first contact portion 112a is formed so as to protrude from the side surface 61q of the proximal end part of the first arm part 61 in the same direction as the direction in which the first protruding portion 64 protrudes. The length of the first contact portion 112a protruding from the side surface 61q is longer than the length of the first protrusion 64 protruding from the side surface 61q. The second contact portion 112b is formed so as to protrude from the side surface 61r of the proximal end part of the first arm part 61 in the same direction as the direction in which the second protruding portion 65 protrudes. The length of the second contact portion 112b protruding from the side surface 61r is longer than the length of the second protrusion 65 protruding from the side surface 61r.

The third contact portion 112c and the fourth contact portion are provided at the proximal end part of the second arm part 62 of the clip body 60, and are disposed on more distal end side than the first protruding portion 66 and the second protruding portion 67. The third contact portion 112c and the fourth contact portion are respectively formed in the same manner as the first contact portion 112a and the second contact portion 112b.

The first contact portion 112a, the second contact portion 112b, the third contact portion 112c, and the fourth contact portion are arranged at the same position in the direction along the longitudinal axis C1. The end coil portion 111a of the coil spring 111 is engaged with each of the first contact portion 112a, the second contact portion 112b, the third contact portion 112c, and the fourth contact portion.

Next, the operation of the pushing mechanism 110 will be described. When the clip body 60 moves toward the proximal end side in the holding tube 70 by pulling the slider 102 of the operation section 100 with respect to the operation section main body 101, the contact section 112 provided on the clip body 60 compresses the coil spring 111 in the direction along the longitudinal axis C1. Here, in a case in which it becomes necessary to grasp the target tissue, when the slider 102 is pushed in, the contact portion 112 is pushed toward the distal end side by the restoring force (biasing force) of the compressed coil spring 111, so that the clip body 60 moves to the distal side together with the operation member 30. In this way, it is possible to grasp the target tissue.

After the first protrusion 64 and the second protrusion 65 of the first arm part 61, and the first protrusion 66 and the second protrusion 67 of the second arm part 62 pass through the inner cavity of the latching part 71 of the holding tube 70, it is impossible to grasp the target tissue. This is because the distal end surface 64p of the first protruding portion 64, the distal end surface 65p of the second protruding portion 65, the distal end surface of the first protruding portion 66, and the distal end surface of the second protruding portion 67 contact the contact surface 70s, so that the clip body 60 is prevented from moving to the distal end side.

Further, when the coil spring 111 is compressed in the direction along the longitudinal axis C1 and the adjacent strands in the coil spring 111 are closely wound, the clip body 60 is prevented from further moving to the proximal end side. Therefore, by appropriately adjusting the position at which the coil spring 111 is closely wound, it is possible to prevent unnecessary force from being applied to the target tissue to be grasped by the first arm part 61 and the second arm part 62 of the clip body 60.

Fourth Modification Example

In the embodiment described above, the hook portion 34 of the connecting member 32 is configured to be elastically deformed or plastically deformed substantially in a straight line when a tensile force of a predetermined magnitude is applied in a direction along the longitudinal axis C1, but it is not limited to this. The connecting member 32 may be configured to release the engagement between the hook portion 34 and the coupling part 63 of the clip body 60 without deformation of the hook portion 34.

Figure 13:
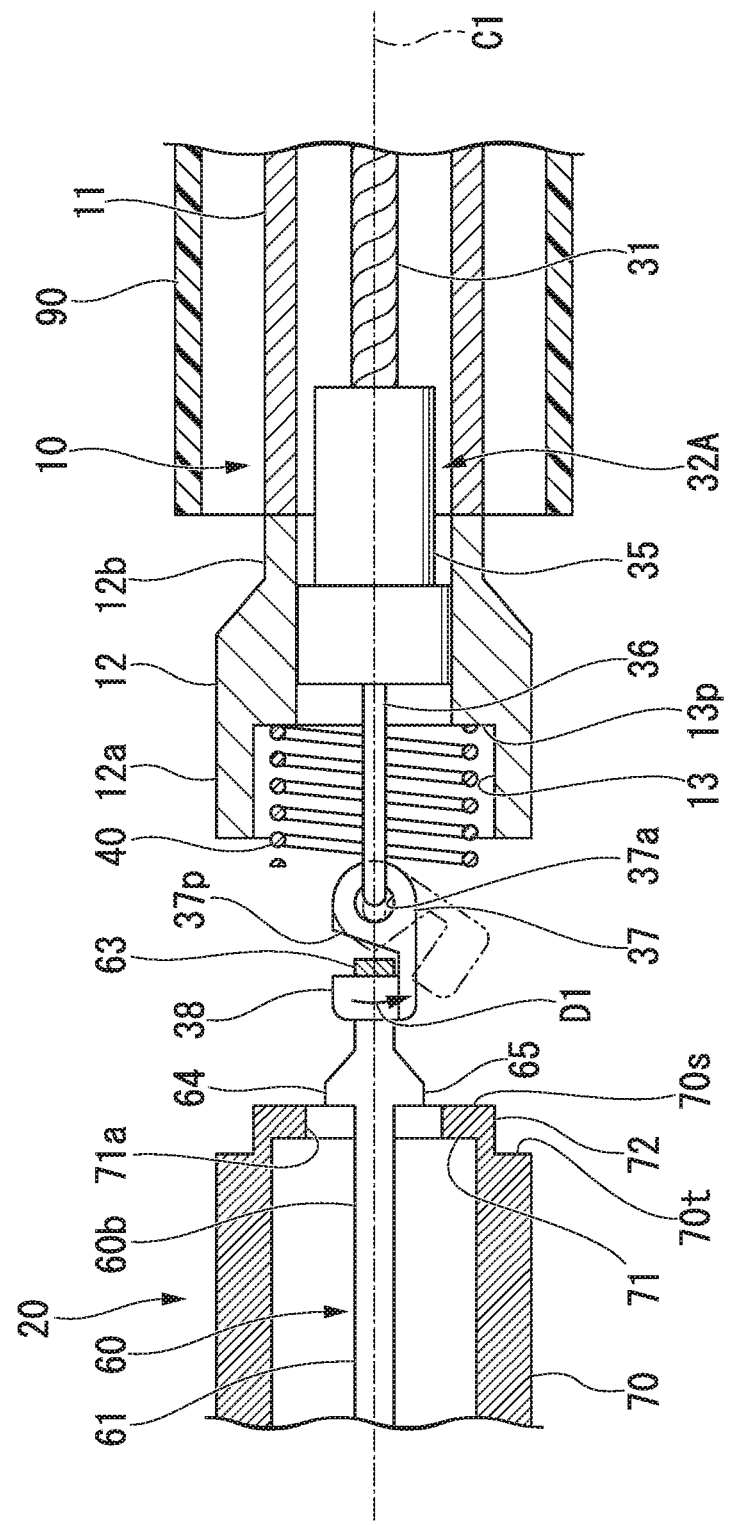
FIG. 13 is a view showing a modified example of the connecting member.

FIG. 13 is a view showing a modified example of the connecting member 32 according to the present embodiment. As shown in FIG. 13, the connecting member 32A of the present modification has a diameter-enlarged portion 35, a loop portion 36, a main body portion 37, and a hook portion 38.

The proximal end part of the diameter-enlarged portion 35 is fixed to the distal end part of the operation wire 31. The diameter-enlarged portion 35 is formed in a cylindrical shape. The outer diameter of the diameter-enlarged portion 35 is set to a dimension that allows the inside of the coil sheath 11 to be inserted.

The loop portion 36 is provided at the distal end part of the diameter-enlarged portion 35. The loop portion 36 is formed by folding a wire. The loop portion 36 is disposed such that the folded back portion of the wire faces the distal end side and both ends of the wire face the proximal end side. Both end parts of the wire in the loop portion 36 are fixed to the distal end part of the diameter-enlarged portion 35 by brazing, welding or the like.

The main body portion 37 has a through hole 37a. The through hole 37a passes through the main body portion 37 along a direction (hereinafter referred to as "first direction") in which the proximal end part of the first arm part 61 and the proximal end part of the second arm part 62 of the clip body 60 are arranged in parallel. In the through hole 37a, the folded back portion of the wire of the loop portion 36 is inserted. Therefore, the main body portion 37 is connected to the loop portion 36 so as to be rotatable around an axis parallel to the first direction. An inclined surface 37p opposed to the hook portion 38 is formed in the main body portion 37. The inclined surface 3'7p is inclined so as to be gradually separated from the hook portion 38 as it goes on from the connecting portion between the main body portion 37 and the hook portion 38 toward the proximal end side.

The hook portion 38 is provided at the distal end part of the main body portion 37 and configured to be rotatable together with the main body portion 37. The hook portion 38 has a shape engageable with the coupling part 63 of the clip body 60. The hook portion 38 can be engaged with the coupling part 63 by disposing the coupling part 63 between the hook portion 38 and the inclined surface 3'7p of the main body portion 37. Further, when the hook portion 38 rotates in the direction D1 with respect to the loop portion 36, the engagement between the hook portion 38 and the coupling part 63 is released.

The loop portion 36, the main body portion 37, and the hook portion 38 have an outer dimension through which the inner cavity of the latching part 71 of the holding tube 70 can be inserted. Further, the outer dimensions of the main body portion 37 and the hook portion 38 are set to be such dimensions that the hook portion 38 is rotated in the direction D1 with respect to the loop portion 36 in a state in which they are disposed inside the holding tube 70 and the engagement between the hook portion 38 and the coupling part 63 is not released.

Next, the operation of releasing the engagement between the hook portion 38 and the coupling part 63 will be described. As shown in FIG. 13, in a state in which the first protrusion 64 and the second protrusion 65 of the first arm part 61, and the first protrusion 66 and the second protrusion 67 of the second arm part 62 pass through the inner cavity of the latching part 71, the main body portion 37 and the hook portion 38 are also located outside the holding tube 70. When the slider 102 of the operation section 100 is pushed in this state, the operation wire 31 moves to the distal end side, and the inclined surface 3'7p of the main body portion 37 contacts the coupling part 63 of the clip body 60. Then, the main body portion 37 and the hook portion 38 are guided by the inclined surface 37p and rotated in the direction D1. As a result, the engagement between the hook portion 38 and the coupling part 63 is released.

Although preferred embodiments of the present invention have been described above, the present invention is not limited to these embodiments. Additions, omissions, substitutions, and other changes in the configuration are possible without departing from the spirit of the present invention.

What is claimed is:

1. An endoscope treatment tool comprises: a sheath having a longitudinal axis and formed in an elongated shape: a clip unit detachably connected to a distal end part of the sheath; an operation member inserted into the sheath so as to be able to advance and retreat and connected to the clip unit; a biasing member; and a first rotation preventing part configured so as to be able to prevent the clip unit from rotating relative to the distal end part of the sheath about the longitudinal axis, wherein the clip unit includes: a clip body having a first arm part and a second arm part which are opposed to each other and whose distal end parts are arranged to be spaced apart from each other, the clip body being connected to the operation member and elastically deformable; a holding tube formed in a cylindrical shape and having a part of the clip body disposed therein; and a second rotation preventing part configured so as to be able to prevent the clip body from rotating relative to the holding tube about the longitudinal axis in an open state in which the first arm part and the second arm part are separated from each other, wherein the biasing member biases the holding tube so as to separate from the distal end part of the sheath, and when a proximal end part of the holding tube comes into contact with the distal end part of the sheath against a biasing force of the biasing member, the first rotation preventing part prevents the relative rotation of the clip unit, wherein the second rotation preventing part has a first notch portion and a second notch portion that are provided at a peripheral edge part on a distal end side of the holding tube the first notch portion and the second notch portion being disposed at portions opposed to each other across the longitudinal axis, the first arm part is arranged to pass through an inside of the first notch portion, the second arm part is arranged to pass through an inside of the second notch portion, and the second rotation preventing part prevents the clip body from relatively rotating with respect to the holding tube about the longitudinal axis in a state in which the first arm and the second arm part are most distant from each other.

2. The endoscopic treatment instrument according to claim 1, wherein
the first rotation preventing part includes:
a first engaging portion having a concave-convex shape and formed on a proximal end surface of the holding tube; and
a second engaging portion having a concave-convex shape and formed on a distal end surface of the sheath, the second engaging portion being engageable with the first engaging portion, and
the proximal end surface of the holding tube contacts the distal end surface of the sheath, whereby the first engaging portion engages with the second engaging portion.

3. The endoscopic treatment instrument according to claim 1, wherein
the first rotation preventing part includes:
a third engaging portion having a concave-convex shape and formed on an outer peripheral surface of the holding tube; and
a fourth engaging portion having a concave-convex shape and formed on an inner peripheral surface of the distal end part of the sheath, the fourth engaging portion being engageable with the third engaging portion, and
the proximal end part of the holding tube enters inside of the distal end part of the sheath, whereby the third engaging portion engages with the fourth engaging portion.

4. The endoscopic treatment instrument according to claim 1, wherein
the first rotation preventing part has a slip prevention member provided on an inner peripheral surface of the distal end part of the sheath, and
the proximal end part of the holding tube enters inside of the distal end part of the sheath, whereby the proximal end part of the holding tube engages with the slip prevention member.

5. The endoscopic treatment instrument according to claim 1, wherein
the biasing member is a coil spring disposed between the distal end part of the sheath and the holding tube.

* * * * *